(12) United States Patent
Ashida et al.

(10) Patent No.: US 6,413,729 B1
(45) Date of Patent: Jul. 2, 2002

(54) PEPTIDOGLYCAN RECOGNITION PROTEINS AND THEIR PRODUCTION

(75) Inventors: Masaaki Ashida; Masanori Ochiai, both of Hokkaido; Masakazu Tsuchiya, Hyogo, all of (JP)

(73) Assignee: Wako Pure Chemical Industries, Inc., Osaka (JP)

( * ) Notice: Subject to any disclaimer, the term of this patent is extended or adjusted under 35 U.S.C. 154(b) by 0 days.

(21) Appl. No.: 09/374,678

(22) Filed: Aug. 16, 1999

Related U.S. Application Data

(62) Division of application No. 08/928,917, filed on Sep. 12, 1997, now Pat. No. 6,034,217.

(30) Foreign Application Priority Data

Sep. 17, 1996 (JP) .............................. 8-244512

(51) Int. Cl.⁷ ........................ G01N 33/566; C12Q 1/04; C07K 14/00
(52) U.S. Cl. ........................ 435/7.32; 435/7.2; 435/34; 530/350; 530/855
(58) Field of Search ................. 435/7.2, 7.32, 435/34; 530/350, 855

(56) References Cited

U.S. PATENT DOCUMENTS

| | | | |
|---|---|---|---|
| 4,596,769 A | * 6/1986 | Shockman et al. ............ | 435/7 |
| 4,970,152 A | 11/1990 | Ashida et al. ................ | 435/19 |
| 5,276,269 A | 1/1994 | Raikhel et al. ............. | 800/205 |

FOREIGN PATENT DOCUMENTS

| | | |
|---|---|---|
| EP | 0 270 039 B1 | 6/1988 |
| EP | 0 657 546 A1 | 11/1994 |
| JP | 7-114707 | 6/1988 |
| WO | WO 97/29765 | 8/1997 |

OTHER PUBLICATIONS

Bowie et al. Deciphering the message in protein sequences: tolerance to amino acid substitutions. Science, (Mar. 16, 1990) 247 (4948) 1306–10.*

Ngo et al., in The Protein Folding Problem and Tertiary Structure Prediction, Merz and Le Grand (Eds), Aug. 1994, Springer Verlag, pp. 433 and 492–495.*

Yoshida et al. "Purification of a Peptidoglycan Recognition Protein from Hemolymph of the Silkworm, Bombyx mori", J. Biol. Chem. 271(23): 13,854–13,860 (1996).

* cited by examiner

*Primary Examiner*—David S. Romeo
(74) *Attorney, Agent, or Firm*—Dike, Bronstein, Roberts & Cushman - IP Group; David G. Colin; Cara Z. Lowan

(57) ABSTRACT

A gene coding for a peptidoglycan recognition peptide (PGRP) is cloned, a recombinant vector into which said gene is introduced is obtained, and a transformant transformed with said recombinant vector is cultivated, thereby producing the PGRP in large amounts at high purity.

1 Claim, 1 Drawing Sheet

Fig. 1

```
         10        20        30        40        50        60        70        80        90       100
CTGACGTGCTGGCACGGCGCCTCTCGACATGGCCCGCCTCCACTCGGCAGTTGTACTCGCTGCTCTCAGTCGTCTTGTTCTCACAGAATAGCAGCCG
                                  M  A  R  L  H  S  A  V  V  L  A  L  S  S  L  L  T  E  I  A  A  D 110       120       130       140       150       160       170       180       190       200
ATTGCGACGTCGTCAGTAAAAAGCAATTGGGACGGTTTGATCCCGGTGCACGTGTCGTCTACCTGGCGCGCCGTGAGCCTCGTCATCGTCCAGCACAGT
 C  D  V  V  S  K  K  Q  W  D  G  L  I  P  V  H  V  S  Y  L  A  R  P  V  S  L  V  I  V  Q  H  T  V 210       220       230       240       250       260       270       280       290       300
CACACCCTTCGAGGACGGACGCTGGTCTGCGAGGAGTCTTGTGCGGAATATCCAGACCAACCACATGGAGGCCTTGCAATACTGGGACATCGGACCCTCG
 T  P  F  C  R  T  D  A  G  C  E  E  L  V  R  N  I  Q  T  N  H  M  E  A  L  Q  Y  W  D  I  G  P  S 310       320       330       340       350       360       370       380       390       400
TTCCTGGTGGGAGGTAACGGCAAGGTGTACGAGGGCTCCGGCTGGCTGCACGTCGGCGCACTACGGCGTACAACTCGAGTCCATCGGAGTCGGAGTCGCAT
 F  L  V  G  G  N  G  K  V  Y  E  G  S  G  W  L  H  V  G  A  H  T  Y  G  Y  N  S  R  S  I  G  V  A  F 410       420       430       440       450       460       470       480       490       500
TCATCGGCAACTTCAACACGGACGAGCCGAGCGGCGATGCTGGAGGCGCTGCGCTCGCGTCGCTGCTGCGCTGCGGCGTGGAGCGCGGCCACCTCGCGGGGA
 I  G  N  F  N  T  D  E  P  S  G  A  M  L  E  A  L  R  S  L  L  R  C  G  V  E  R  G  H  L  A  G  D 510       520       530       540       550       560       570       580       590       600
CTACCGGGTCGTGGCCCACCGACAGCTTCATTGCCTCTGAGAGCCCCGGCGAAGCTCTACAACCAGATACGCCGCTGGCCTGAGTGGCTGGAGAAGTG
 Y  R  V  V  A  H  R  Q  L  I  A  S  E  S  P  G  R  K  L  Y  N  Q  I  R  R  W  P  E  W  L  E  N  V 610       620       630       640       650       660       670       680       690       700
GACTCCATCAAGAACGCGTAACATTATCACAGGGTATCGCATAGCGCCGTTCTTGTTGTTCAGATCTTGGACAAGTGTCAACTCATATAGTATTTACG
 D  S  I  K  N  A  *

710       720       730       740       750       760
CGTAATATAATTAAACTACTTATAAATTAAAAAAAAAAAAAAAAAAAAAA
```

PEPTIDOGLYCAN RECOGNITION PROTEINS AND THEIR PRODUCTION

This application is a divisional of U.S. application Ser. No. 08/928,917, filed Sep. 12, 1997 now U.S. Pat. No. 6,034,217, the teachings of which are incorporated herein by reference.

FIELD OF THE INVENTION

The present invention directs to peptidoglycan recognition proteins (hereinafter also briefly referred to as PGRPs), genes coding for said proteins, recombinant vectors containing said genes, transformants transformed with said recombinant vectors, a method for preparing said proteins by cultivating said transformants.

BACKGROUND OF THE INVENTION

Peptidoglycans (hereinafter also briefly referred to as PGs) are glycopeptide polymers containing N-acetylmuramic acid or N-glycolylmuramic acid and D-amino acids, and they play, as bacterial cell wall components, an important role for retention of the form of bacteria.

While endotoxins are contained only in Gram-positive bacteria, peptideglycans are contained both in Gram-negative and Gram-positive bacteria. Namely, in the Gram-negative bacteria, the peptidoglycans are contained in the cell walls to form thick layers at the outermost shells of the cell walls, and in the Gram-positive bacteria, they are contained in the cell walls to form thin layers inside outer membranes of the cell walls. This means that almost all procaryotes contain peptidoglycans in their cell walls, only exception being archaebacteria (such as methane bacteria and high acidophil thermophiles) which contain no endotoxins nor peptidoglycan. On the sharp contrary, eucaryotes such as mammals contain no peptidoglycans in their cell walls.

Thus peptidoglycans can be said as an useful indicator for existence of bacteria in various kinds of objects.

Accordingly, a trace amount of bacteria contained in various kinds of objects can be detected by subjecting the objects to detection and measurement of peptidoglycans. The detection and measurement of peptidoglycans are therefore expected to be applied to safety tests of drugs, microbial tests of water and food, and diagnoses of infectious diseases.

The chemical structures of peptidoglycans are classified to into several kinds although they vary with bacteria species. For example, peptide sub-units each consisting of 3 or 4 amino acids are attached through the carboxyl groups of muramic acid molecules to a saccharide chain having the repeating structure of N-acetylglucosamine and N-acetylmuramic acid which are linked by a β-1,4 bond to each other, and the peptide sub-units are crosslinked directly or through other peptides, thereby forming a network structure in a bag form as a whole.

The peptidoglycans have various biological activities. Examples thereof in vitro include various functions to immune response cells such as macrophages, B lymphocytes and T lymphocytes, destruction of blood platelets, growth enhancement of fibroblasts, enhancement of bone resorption and activation of complements. Examples thereof in vivo include enhancement or inhibition of humoral immune responses, enhansment of cellular immunity, stimulation of cell endothelial systems, transient leukopenia and subsequent hypercytosis, enhancing the functions of interferon inducing factors, potentiation of natural resistance, induction of experimental autoimmune diseases, pyrogenic functions, enhancing sensitivity to the toxicity of endotoxins, enhancement or inhibition of sleep, formation of epithelioid granulomas, functions of inducing hemorrhagic necrotics at sites treated with tubercle bacillus, and acute or chronic toxicity. Many of these activities are in common with the functions of endotoxins, and weaker in intensity than the endotoxins. However, detection and measurement of peptidoglycans contained, for example, in drugs or food are considered to become increasingly important from now on, because of such activities of the peptidoglycans.

As a method for detecting and measuring peptidoglycans, a method developed by the present inventors in which a silkworm hemolymph-derived reagent is used is reported in Japanese Examined Patent Publication No. 7-114707. According to this method, it is possible to measure the total PG content in a sample. However, it is impossible, for example, to test the PG distribution in a solid such as a tissue section, or to conduct a specific stain of bacteria in a tissue section.

Accordingly, the development of a method for specifically detecting and measuring PGs which can be used for such purposes has been desired.

Such a method for specifically detecting and measuring PGs has been considered to be accomplished by using substances specifically binding to the PGs. However, no substance having preferable properties is available at low cost in large amounts, so that no practical method has been developed yet.

Namely, as the substances specifically binding to the PGs, for example, lysozyme and the peptidoglycan recognition protein discovered by the present inventors [*J. Bio. Chem.* 271 (23), 13854–13860 (1992)] are known. However, lysozyme is an enzyme which decomposes the PGs by binding to them, so that it is unsuitable for use for such purposes. On the other hand, the peptidoglycan recognition protein is only obtained by purification from hemolymph of insects such as silkworms, in which it is contained in very small amounts. In respect to cost, therefore, it is hard to say that a reagent using this peptidoglycan recognition protein is practical.

Accordingly, the development of a method for obtaining the peptidoglycan recognition proteins at low cost in large amounts has been desired.

SUMMARY OF THE INVENTION

It is therefore an object of the present invention to provide a method for obtaining peptidoglycan recognition proteins in large amounts at high purity.

As a result of intensive investigation for attaining the above-mentioned object, the present inventors have succeeded in elucidating the primary structure of PGRPs to clone cDNA coding for PGRPs, determining amino acid sequences of the PGRPs based on a nucleotide sequence of the cDNA, and producing the PGRPs by recombinant technology using the DNA, thereby attaining the above-mentioned object.

That is, the present invention provides:

(1) A recombinant protein comprising the following amino acid sequence (SEQ ID NO: 1):
Asp Cys Asp Val Val Ser Lys Lys Gln Trp Asp Gly Leu Ile Pro Val His Val Ser Tyr Leu Ala Arg Pro Val Ser Leu Val Ile Val Gln His Thr Val Thr Pro Phe Cys Arg Thr Asp Ala Gly Cys Glu Glu Leu Val Arg Asn Ile Gln Thr Asn His Met Glu Ala Leu Gln Tyr Trp Asp Ile Gly Pro Ser Phe Leu Val Gly Gly Asn Gly Lys Val Tyr Glu Gly Ser Gly Trp Leu His Val Gly Ala His Thr Tyr Gly Tyr Asn Ser Arg Ser Ile Gly Val Ala Phe Ile Gly Asn Phe Asn Thr Asp Glu Pro Ser Gly Ala Met Leu Glu Ala Leu Arg Ser Leu Leu Arg Cys Gly Val Glu Arg Gly His Leu Ala Gly Asp Tyr Arg Val Val Ala His Arg Gln Leu Ile Ala Ser Glu Ser Pro Gly Arg Lys Leu Tyr Asn Gln Ile Arg Arg Trp Pro Glu Trp Leu Glu Asn Val Asp Ser Ile Lys Asn Ala;

(2) the recombinant protein according to (1), wherein the recombinant protein has peptidoglycan recognition activity and has the following amino acid sequence (SEQ ID NO:1) or one obtained by deletion, substitution or addition of one or more amino acids in the following amino acid sequence (SEQ ID NO:1):
Asp Cys Asp Val Val Ser Lys Lys Gln Trp Asp Gly Leu Ile Pro Val His Val Ser Tyr Leu Ala Arg Pro Val Ser Leu Val Ile Val Gln His Thr Val Thr Pro Phe Cys Arg Thr Asp Ala Gly Cys Glu Glu Leu Val Arg Asn Ile Gln Thr Asn His Met Glu Ala Leu Gln Tyr Trp Asp Ile Gly Pro Ser Phe Leu Val Gly Gly Asn Gly Lys Val Tyr Glu Gly Ser Gly Trp Leu His Val Gly Ala His Thr Tyr Gly Tyr Asn Ser Arg Ser Ile Gly Val Ala Phe Ile Gly Asn Phe Asn Thr Asp Glu Pro Ser Gly Ala Met Leu Glu Ala Leu Arg Ser Leu Leu Arg Cys Gly Val Glu Arg Gly His Leu Ala Gly Asp Tyr Arg Val Val Ala His Arg Gln Leu Ile Ala Ser Glu Ser Pro Gly Arg Lys Leu Tyr Asn Gln Ile Arg Arg Trp Pro Glu Trp Leu Glu Asn Val Asp Ser Ile Lys Asn Ala;

(3) a gene coding for a protein comprising the following amino acid sequence (SEQ ID NO:1):
Asp Cys Asp Val Val Ser Lys Lys Gln Trp Asp Gly Leu Ile Pro Val His Val Ser Tyr Leu Ala Arg Pro Val Ser Leu Val Ile Val Gln His Thr Val Thr Pro Phe Cys Arg Thr Asp Ala Gly Cys Glu Glu Leu Val Arg Asn Ile Gln Thr Asn His Met Glu Ala Leu Gln Tyr Trp Asp Ile Gly Pro Ser Phe Leu Val Gly Gly Asn Gly Lys Val Tyr Glu Gly Ser Gly Trp Leu His Val Gly Ala His Thr Tyr Gly Tyr Asn Ser Arg Ser Ile Gly Val Ala Phe Ile Gly Asn Phe Asn Thr Asp Glu Pro Ser Gly Ala Met Leu Glu Ala Leu Arg Ser Leu Leu Arg Cys Gly Val Glu Arg Gly His Leu Ala Gly Asp Tyr Arg Val Val Ala His Arg Gln Leu Ile Ala Ser Glu Ser Pro Gly Arg Lys Leu Tyr Asn Gln Ile Arg Arg Trp Pro Glu Trp Leu Glu Asn Val Asp Ser Ile Lys Asn Ala;

(4) the gene according to (3), wherein the protein has peptidoglycan recognition activity and has the following amino acid sequence (SEQ ID NO:1) or one obtained by deletion, substitution or addition of one or more amino acids in the following amino acid sequence (SEQ ID NO: 1):
Asp Cys Asp Val Val Ser Lys Lys Gln Trp Asp Gly Leu Ile Pro Val His Val Ser Tyr Leu Ala Arg Pro Val Ser Leu Val Ile Val Gln His Thr Val Thr Pro Phe Cys Arg Thr Asp Ala Gly Cys Glu Glu Leu Val Arg Asn Ile Gln Thr Asn His Met Glu Ala Leu Gln Tyr Trp Asp Ile Gly Pro Ser Phe Leu Val Gly Gly Asn Gly Lys Val Tyr Glu Gly Ser Gly Trp Leu His Val Gly Ala His Thr Tyr Gly Tyr Asn Ser Arg Ser Ile Gly Val Ala Phe Ile Gly Asn Phe Asn Thr Asp Glu Pro Ser Gly Ala Met Leu Glu Ala Leu Arg Ser Leu Leu Arg Cys Gly Val Glu Arg Gly His Leu Ala Gly Asp Tyr Arg Val Val Ala His Arg Gln Leu Ile Ala Ser Glu Ser Pro Gly Arg Lys Leu Tyr Asn Gln Ile Arg Arg Trp Pro Glu Trp Leu Glu Asn Val Asp Ser Ile Lys Asn Ala;

(5) a gene coding for a protein comprising the following amino acid sequence (SEQ ID NO: 2)
Met Ala Arg Leu His Ser Ala Val Val Leu Ala Leu Ala Leu Ser Ser Leu Leu Thr Glu Ile Ala Ala Asp Cys Asp Val Val Ser Lys Lys Gln Trp Asp Gly Leu Ile Pro Val His Val Ser Tyr Leu Ala Arg Pro Val Ser Leu Val Ile Val Gln His Thr Val Thr Pro Phe Cys Arg Thr Asp Ala Gly Cys Glu Glu Leu Val Arg Asn Ile Gln Thr Asn His Met Glu Ala Leu Gln Tyr Trp Asp Ile Gly Pro Ser Phe Leu Val Gly Gly Asn Gly Lys Val Tyr Glu Gly Ser Gly Trp Leu His Val Gly Ala His Thr Tyr Gly Tyr Asn Ser Arg Ser Ile Gly Val Ala Phe Ile Gly Asn Phe Asn Thr Asp Glu Pro Ser Gly Ala Met Leu Glu Ala Leu Arg Ser Leu Leu Arg Cys Gly Val Clu Arg Gly His Leu Ala Gly Asp Tyr Arg Val Val Ala His Arg Gln Leu Ile Ala Ser Glu Ser Pro Gly Arg Lys Leu Tyr Asn Gln Ile Arg Arg Trp Pro Glu Trp Leu Glu Asn Val Asp Ser Ile Lys Asn Ala;

(6) the gene according to (5), wherein the protein has peptidoglycan recognition activity and has the following amino acid sequence (SEQ ID NO:2) or one obtained by deletion, substitution or addition of one or more amino acids in the following amino acid sequence (SEQ ID NO: 2):
Met Ala Arg Leu His Ser Ala Val Val Leu Ala Leu Ala Leu Ser Ser Leu Leu Thr Glu Ile Ala Ala Asp Cys Asp Val Val Ser Lys Lys Gln Trp Asp Gly Leu Ile Pro Val His Val Ser Tyr Leu Ala Arg Pro Val Ser Leu Val Ile Val Gln His Thr Val Thr Pro Phe Cys Arg Thr Asp Ala Gly Cys Glu Glu Leu Val Arg Asn Ile Gln Thr Asn His Met Glu Ala Leu Gln Tyr Trp Asp IIe Gly Pro Ser Phe Leu Val Gly Gly Asn Gly Lys Val Tyr Glu Gly Ser Gly Trp Leu His Val Gly Ala His Thr Tyr Gly Tyr Asn Ser Arg Ser Ile Gly Val Ala Phe Ile Gly Asn Phe Asn Thr Asp Glu Pro Ser Gly Ala Met Leu Glu Ala Leu Arg Ser Leu Leu Arg Cys Gly Val Glu Arg Gly His Leu Ala Gly Asp Tyr Arg Val Val Ala His Arg Gln Leu Ile Ala Ser Glu Ser Pro Gly Arg Lys Leu Tyr Asn Gln Ile Arg Arg Trp Pro Glu Trp Leu Glu Asn Val Asp Ser Ile Lys Asn Ala;

(7) a gene comprising a DNA having the following
nucleotide sequence (SEQ ID NO: 3):
GATTGCGACGTCGTCAGTAAAAAGCAATGGGACGGTTTGATCCCGGTGCACGTGTCGTACCTG

GCGCGGCCCGTGAGCCTCGTCATCGTCCAGCACACAGTCACACCCTTCTGCAGGACGGACGCT

GGCTGCGAGGAGCTCGTGCGGAATATCCAGACCAACCACATGGAGGCCTTGCAATACTGGGAC

ATCGGACCCTCGTTCCTGGTGGGAGGTAACGGCAAGGTGTACGAGGGCTCCGGCTGGCTGCAC

GTCGGCGCGCACACCTACGGGTACAACTCGAGGTCCATCGGAGTCGCATTCATCGGCAACTTC

AACACGGACGAGCCGAGCGGCGCGATGCTGGAGGCGCTGCGGTCGCTGCTGCGCTGCGGCGTG

GAGCGCGGCCACCTCGCGGGGGACTACCGCGTCGTGGCGCACCGACAGCTCATTGCCTCTGAG

AGCCCCGGCCGGAAGCTCTACAACCAGATACGACGCTGGCCTGAGTGGCTGGAGAACGTGGAC

TCCATCAAGAACGCGTAA;

(8) a gene comprising a DNA including a nucleotide
sequence which codes a protein having peptidoglycan recognition
activity and is capable of hybridizing with the DNA having the
following nucleotide sequence (SEQ ID NO: 3) under stringent
conditions:
GATTGCGACGTCGTCAGTAAAAAGCAATGGGACGGTTTGATCCCGGTGCACGTGTCGTACCTG

GCGCGGCCCGTGAGCCTCGTCATCGTCCAGCACACAGTCACACCCTTCTGCAGGACGGACGCT

GGCTGCGAGGAGCTCGTGCGGAATATCCAGACCAACCACATGGAGGCCTTGCAATACTGGGAC

ATCGGACCCTCGTTCCTGGTGGGAGGTAACGGCAAGGTGTACGAGGGCTCCGGCTGGCTGCAC

GTCGGCGCGCACACCTACGGGTACAACTCGAGGTCCATCGGAGTCGCATTCATCGGCAACTTC

AACACGGACGAGCCGAGCGGCGCGATGCTGGAGGCGCTGCGGTCGCTGCTGCGCTGCGGCGTG

GAGCGCGGCCACCTCGCGGGGGACTACCGCGTCGTGGCGCACCGACAGCTCATTGCCTCTGAG

AGCCCCGGCCGGAAGCTCTACAACCAGATACGACGCTGGCCTGAGTGGCTGGAGAACGTGGAC

TCCATCAAGAACGCGTAA;

(9) a gene comprising a DNA having the following
nucleotide sequence (SEQ ID NO: 5):
ATGGCCCGCCTCCACTCGGCAGTTGTACTCGCGCTCGCTCTCAGCTCGCTTCTCACAGAAATA

GCAGCCGATTGCGACGTCGTCAGTAAAAAGCAATGGGACGGTTTGATCCCGGTGCACGTGTCG

TACCTGGCGCGGCCCGTGAGCCTCGTCATCGTCCAGCACACAGTCACACCCTTCTGCAGGACG

GACGCTGGCTGCGAGGAGCTCGTGCGGAATATCCAGACCAACCACATGGAGGCCTTGCAATAC

TGGGACATCGGACCCTCGTTCCTGGTGGGAGGTAACGGCAAGGTGTACGAGGGCTCCGGCTGG

CTGCACGTCGGCGCGCACACCTACGGGTACAACTCGAGGTCCATCGGAGTCGCATTCATCGGC

AACTTCAACACGGACGAGCCGAGCGGCGCGATGCTGGAGGCGCTGCGGTCGCTGCTGCGCTGC

GGCGTGGAGCGCGGCCACCTCGCGGGGGACTACCGCGTCGTGGCGCACCGACAGCTCATTGCC

TCTGAGAGCCCCGGCCGGAAGCTCTACAACCAGATACGACGCTGGCCTGAGTGGCTGGAGAAC

GTGGACTCCATCAAGAACGCGTAA;

(10) a gene comprising a DNA including a nucleotide
sequence which codes a protein having peptidoglycan recognition
activity and is capable of hybridizing with the DNA having the
following nucleotide sequence (SEQ ID NO: 5) under stringent
conditions:
ATGGCCCGCCTCCACTCGGCAGTTGTACTCGCGCTCGCTCTCAGCTCGCTTCTCACAGAAATA

GCAGCCGATTGCGACGTCGTCAGTAAAAAGCAATGGGACGGTTTGATCCCGGTGCACGTGTCG

-continued

```
TACCTGGCGCGGCCCGTGAGCCTCGTCATCGTCCAGCACACAGTCACACCCTTCTGCAGGACG

GACGCTGGCTGCGAGGAGCTCGTGCGGAATATCCAGACCAACCACATGGAGGCCTTGCAATAC

TGGGACATCGGACCCTCGTTCCTGGTGGGAGGTAACGGCAAGGTGTACGAGGGCTCCGGCTGG

CTGCACGTCGGCGCGCACACCTACGGGTACAACTCGAGGTCCATCGGAGTCGCATTCATCGGC

AACTTCAACACGGACGAGCCGAGCGGCGCGATGCTGGAGGCGCTGCGGTCGCTGCTGCGCTGC

GGCGTGGAGCGCGGCCACCTCGCGGGGGACTACCGCGTCGTGGCGCACCGACAGCTCATTGCC

TCTGAGAGCCCCGGCCGGAAGCTCTACAACCAGATACGACGCTGGCCTGAGTGGCTGGAGAAC

GTGGACTCCATCAAGAACGCGTAA;
```

(11) a recombinant vector comprising the gene of (3),
(5), (7) or (9),
(12) a transformant transformed with the recombinant
vector of (11); and
(13) a method for producing a peptidoglycan recognition
protein comprising cultivating the transformant of (12) in a
broth, and recovering the peptidoglycan recognition protein
from the culture.

BRIEF DESCRIPTION OF THE DRAWING

FIG. 1 shows a nucleotide sequence of a PGRP cDNA clone (SEQ ID NO: 7) obtained in the present invention, and an amino acid sequence (SEQ ID NO: 8) deduced therefrom.

DESCRIPTION OF THE PREFERRED EMBODIMENTS

The PGRP of the present invention is the protein comprising the amino acid sequence of SEQ ID NO: 1, and the polypeptide comprising the amino acid sequence obtained by deletion, substitution or addition of one or more amino acids in the amino acid sequence of SEQ ID NO: 1, as well as the polypeptide comprising the amino acid sequence of SEQ ID NO: 1, is included in the scope of the present invention, as long as it has polypeptidoglycan recognition activity. There is no particular limitation on its origin, and PGRPs derived from insects other than silkworms are included in the scope of the present invention. The insects other than silkworms include, for example, lepidoptera such as hornworms, diptera such as flesh fly and houseflies, orthoptera such as migratory locusts and Emma field crickets, and coleoptera such as Acalolepa luxuriosa.

The term "peptidoglycan recognition activity" as used herein means the ability to specifically bind to a peptidoglycan, and it can be measured, for example, in Eaccordance with the method described in *J. Bio. Chem.* 271 (23), 13855 (1992) (refer to Reference Example given below).

The gene coding for the PGRP of the present invention may be any, as long as it is a DNA coding for the polypeptide containing the above-mentioned amino acid sequence, and further includes mRNA which is a transcribed product thereof. Examples of the genes include genes comprising the DNA sequence represented by SEQ ID NO: 3, and genes comprising the DNA sequence represented by SEQ ID NO: 5 (a nucleotide sequence coding for a polypeptide containing the amino acid sequence of SEQ ID NO: 2 having a pro portion, which is given below). The DNA hybridizing with the DNA having the above-mentioned nucleotide sequence under stringent conditions and containing the nucleotide sequence coding for the protein having peptidoglycan recognition activity is also included in the scope of the present invention. The stringent conditions used in the present invention means conditions to be able to hybridize at 42° C. in 50% formamide, 0.5% SDS and 2×PIPES (0.8 M NaCl, 20 mM PIPES buffer, pH 6.5), preferably to be able to hybridize even after washing at 58° C. in 0.1×SSC(NaCl-citric acid buffer) including 0.1% SDS). There is no particular limitation on the origin of the gene and the gene coding for the PGRP derived from insects other than silkworms are also included in the scope of the present invention. The insects other than silkworms include, for example, lepidoptera such as hornworms, diptera. such as flesh fly and houseflies, orthoptera such as migratory locusts and Emma field crickets, and coleoptera such as acalolepa luxuriosa.

The DNAs of the present invention may be obtained by any methods. Examples of the DNAs include complementary DNA (cDNA) prepared from mRNA, DNA prepared from genome DNA, DNA obtained by chemical synthesis and DNA constructed by an appropriate combination thereof.

mRNA of the PGRP has an RNA sequence corresponding to the nucleotide sequence of the DNA coding for the PGRP, and has a sequence in which thymine is substituted by uracil in the nucleotide sequence of the DNA.

The DNA coding for the PGRP of the present invention can be obtained by a, method of cloning cDNA from mRNA of said polypeptide, a method of isolating the DNA from PGRP genome DNA, a chemical synthesis method or the like.

(1) For example, the following method is shown as the method of cloning CDNA from mRNA of the PGRP. First, a fat body is collected from silkworm larvae, and mRNA coding for silkworm PGRP is obtained from the fat body by a known method such as the guanidine thiocyanate method [J. M. Chirgwin et al., *Biochem.* 18, 5294 (1979)] or by use of a commercial kit (for example, an ISOGEN kit (Nippon Gene). Using the resulting mRNA as a template, a cDNA chain is synthesized by a known method such as a method of using reverse transcriptase, which includes, for example, the method of H. Okayama et al. [H. Okayama et al., *Mol. Cell. Biol.* 2, 161 (1982); ibid. 3, 280 (1983)] or the method of U. Gubler and B. J. Hoffman [U. Gubler and B. J. Hoffman, *Gene* 25, 263 (1983)], and is converted to double stranded cDNA [Y. Maniatis et al., *Cell* 8, 163 (1976)]. The resulting cDNA fragment is introduced into a plasmid vector or a phage vector, thereby constructing a silkworm fat body cDNA library. These processes may be carried out by use of a commercial kit (for example, a ZAP cDNA synthesis kit (Stratagene). There is no particular limitation on the plasmid vector used herein, as long as it is replicable and retainable in a host, and the phage vector used herein may be any, as long as it is self-reproducable in a host. However, when subjected to immunological screening described below, it is required to be a vector having a promoter which can express a PGRP gene in a host.

Methods for introducing the DNA into the plasmid include, for example, the method described in T. Maniatis et al., *Molecular Cloninq, A Laboratory Manual* 1, 82, Cold Spring Harbor Laboratory (1982). Methods for introducing the DNA into the phage vector include, for example, the method of T. V.

Hyunh et al. [*DNA Cloning, A Practical Approach* 1, 49 (1985)]. The recombinant plasmid or the phage vector thus obtained is introduced into an appropriate host such as a procaryotic cell or an eucaryotic cell.

Methods for introducing the plasmid into the host include the calcium chloride method and the calcium chloride/rubidium chloride method described in T. Maniatis et al., *Molecular Cloning, A Laboratory Manual* 1, 82, Cold Spring Harbor Laboratory (1982). Further, methods for introducing the phage vector into the host include a method of introducing phage DNA into a proliferated host after in vitro packaging.

Methods for isolating the DNA coding for the PGRP from the DNA library constructed by the above-mentioned method include the following methods.

For example, an oligonucleotide considered to correspond to a partial amino acid sequence of the PGRP is synthesized. Then, the oligonucleotide is labeled with $^{32}$P to prepare a probe, and a clone having the target DNA is selected by the known colony hybridization method [M. Crunstein and D. S. Hogness, *Proc. Natl. Acad. Sci. U.S.A.* 72, 3961 (1975)] or plaque hybridization method [*Molecular Cloning, A Laboratory Manual* 1, 82, Cold Spring Harbor Laboratory, (1982)]. There are also a method of selecting a clone having the target DNA by use of an antibody to the PGRP utilizing the antigen-antibody reaction, and a method of amplifying a specified region of the PGRP gene by use of the polymerase chain reaction method (PCR method) to isolate the PGRP gene. When the entire region of the gene is not obtained as a result of isolation, the cDNA library is screened again by colony hybridization or plaque hybridization using the isolated DNA fragment or a part thereof as a probe, whereby the entire gene region can finally be obtained.

The nucleotide sequence of the DNA thus obtained can be determined by Maxam-Gilbert method [A. M. Maxam and W. Gilbert, *Proc. Natl. Acad. Sci. U.S.A.* 74, 560 (1977)] or the dideoxynucleotide-chain termination method [J. Messing et al., *Nucleic Acid Res.* 9, 309 (1981)] to confirm the presence of the PGRP gene. The PGRP gene can be obtained by a digestion with a restriction enzyme from the clone thus obtained.

(2) The preparation methods by isolating the DNA coding for the PGRP from the genome DNA of the silkworm fat body include, for example, the following method. The silkworm fat body is dissolved(digested) preferably by use of SDS or proteinase K, and extraction with phenol is repeated to deproteinize the DNA. RNA is digested preferably with RNase. The DNA thus obtained is partially digested with an appropriate enzyme, and the resulting DNA fragment is amplified in an appropriate phage or cosmid. Then, a clone having the target sequence is detected, for example, by a method using a DNA probe labeled with a radioisotope, and the PGRP gene can be obtained by a digestion with a restriction enzyme from said clone.

(3) Further, an oligonucleotide considered to correspond to a partial amino acid sequence of the PGRP is chemically synthesized. Then, the oligonucleotide is labeled with $^{32}$P to prepare a probe, which is hybridized with a digested product of the PGRP genome DNA prepared in the same manner as with (2) described above with a restriction enzyme such as BamHI, by Southern blotting, thereby preparing a restriction enzyme map in the vicinity of the target gene.

The PGRP genome DNA thus prepared is digested with an appropriate restriction enzyme to subject the DNA to fragmentation. The DNA fragments are fractionated by molecular weight fractionation such as gel electrophoresis or gel filtration to obtain fractions comprising the target gene-containing DNA fragments with reference to the restriction enzyme map prepared. The group of DNA fragments thus obtained are introduced into plasmid vectors or phage vectors, thereby constructing a restricted PGRP genome DNA library.

A clone containing the DNA coding for the PGRP is selected by the colony hybridization method or the. plaque hybridization method using the above-mentioned probe labeled with $P^{32}$. There are also a method of selecting a clone having the target DNA by use of an antibody to said polypeptide utilizing the antigen-antibody reaction, and a method of amplifying a specified region of the polypeptide gene by use of the polymerase chain reaction method (PCR method) to isolate said polypeptide gene. When the entire region of said polypeptide gene isolated is not obtained, the PGRP genome DNA library is subjected to Southern blot hybridization as described above, using the isolated DNA fragment or a part thereof as a probe, and the PGRP genome DNA fragment containing the remainder of the target gene is deduced from a group of DNA fragments obtained by digestion with various other restriction enzymes. Using the group of DNA fragments fractionated and obtained by the above-mentioned method, a PGRP genome DNA library is constructed again, and a clone containing the target DNA is selected using the isolated DNA fragment or a part thereof as a probe, whereby the entire gene region can finally be obtained. The PGRP polypeptide gene can be obtained by a digestion with a restriction enzyme from the clone thus obtained.

Further, the present invention provides a recombinant vector containing the DNA coding for the above-mentioned PGRP polypeptide.

There is no particular limitation on said recombinant vector, as long as it contains the DNA coding for the above-mentioned PGRP polypeptide, and is replicable and retainable or self-reproducable in various hosts of procaryotic cells and/or eucaryotic cells. Such vectors include vectors constructed by the known constructing methods of the recombinant vectors (for example, [*Molecular Cloning, A Laboratory Manual* 1, 82, Cold Spring Harbor Laboratory, (1982), etc.].

There is no particular limitation on a vector used when the recombinant vector of the present invention is constructed, as long as it is replicable and retainable or self-reproducable in various hosts of procaryotic cells and/or eucaryotic cells such as plasmid vectors and phage vectors. Examples thereof include natural plasmids, artificially modified plasmids (DNA fragments prepared from natural plasmids) and synthetic plasmids.

The recombinant vector of the present invention can also be prepared simply by introducing the DNA coding for the polypeptide into a vector available in this field in the usual way. Examples of such vectors include *Escherichia coli*-derived plasmids such as pBR322, pBR325, pUC12, pUC13 and pBluescript, yeast-derived plasmids such as pSH19 and pSH15, and *Bacillus subtilis*-derived plasmids such as pUB110, pTP5 and pC194. Further, examples of the phage vectors include bacteriophages such as λ phage, and viruses, which infect to animals and insects, such as retroviruses, vaccinia viruses and nuclear polyhedrosis viruses (for example, Baculovirus and etc.). Preferred examples of the vectors include plasmid vectors, bacteriophage vectors and nuclear polyhedrosis viruses vectors.

In order to attain the object of expressing the DNA coding for the PGRP polypeptide to produce the protein, it is desirable to introduce said DNA into an expression vector when the recombinant vector of the present invention is constructed.

There is no particular limitation on these vectors, as long as they are replicable and retainable or self-reproducable in various hosts of procaryotic cells and/or eucaryotic cells, and have the function of expressing PGRP DNAs in the various hosts of procaryotic cells and/or eucaryotic cells, in other words, the function of producing the target proteins.

When the host cell is *E. coli.*, preferred examples of such expression vectors available in this field include pBR322, pUC12, pUC13, pTrcHis, pMAL-c2, pMAL-p2 and artificially modified vectors (DNA fragments obtained by treating said vectors with restriction enzymes). When the host cell is yeast, preferred examples thereof include plasmids pRS403, pRS404, pRS413, pRS414 and pYES2. When the host cell is an animal cell, preferred examples thereof include plasmids pRSVneo ATCC 37198, pSV2dhfr ATCC 37145, pdBPV-MMTneo ATCC 37224 and pSV2neo ATCC 37149. When the host cell is an insect cell, preferred examples thereof include *Autographica californica* nuclear polyhedrosis virus (AcNPV) and *Bombyx mori* nuclear polyhedrosis virus (BmNPV).

When a bacterium, particularly *E. coli.* is used as the host cell, the recombinant vector of the present invention generally contains a promoter-operator region, an initiation codon, a DNA coding for the PGRP of the present invention, a termination codon, a terminator region or the like.

Further, when yeast or an animal cell is used as the host cell, the recombinant vector of the present invention generally contains a promoter, an initiation codon, a DNA coding for the PGRP of the present invention, a termination codon or the like. Into the recombinant vector may be optionally introduced a DNA coding for a signal peptide, an enhancer sequence or a non-translation region on the 5'- or 3'-terminal side of the PGRP of the present invention.

The promoter-operator region for expressing the PGRP of the present invention in a bacterium includes a promoter, an operator and a Shine-Dalgarno (SD) sequence (for example, AAGG). For example, when the host cell is Escherichia, a Trc (trp-lac) promoter, a Tac promoter, a Trp promoter, a lac promoter, a recA promoter, a λPL promoter or a lpp promoter is suitably used. The promoters for expressing the PGRP of the present invention in yeast include a PHO5 promoter, a PGK promoter, a GAP promoter, an ADH promoter and an AOX1 promoter. When the host cell is Bacillus, the promoters include an SLO1 promoter, an SPO2 promoter and a penp promoter. Further, when the host cell is an eucaryotic cell such as an animal cell, the promoters include an SV40-derived promoter, a retrovirus promoter and a nuclear polyhedrosis virus promoter. However, the promoters are not limited thereto.

For expression, a method in which isopropyl-β-D-thiogalactoside (IPTG) or methanol is added to induce expression, or use of an enhancer is an effective method.

Preferred examples of the initiation codons include a methionine codon (ATG).

Examples of the termination codons include termination codons of common use (for example, TAG and TGA).

The terminator regions include natural and synthetic terminators. Examples of the enhancer sequences include an enhancer sequence (72 bp) of SV40, DNA oncogenic viruses such as polyoma, adeno and papilloma viruses, retrovirus long terminal repeat (LTR), immunoglobulin H chain and L chain gene-derived sequences. The expression vector can be prepared by binding the promotor, the initiation codon, the DNA coding for the PGRP of the present invention, the termination codon and the terminator region successively and cyclically to an appropriate replicable unit. In this case, an appropriate DNA fragment (for example, a linker) can be optionally used according to conventional methods such as digestion with a restriction enzyme and ligation using T4 DNA ligase.

The transformant of the present invention (hereinafter aused as the concept including a transductant) can be prepared by introducing the above-mentioned expression vector into a host cell.

The host cells include a procaryotic cell and an eucaryotic cell.

Concrete examples of the host cells include microorganisms such as bacteria (for example, Escherichia and Bacillus), yeast (for example, Saccharomyces and Pichia), animal cells and insect cells. Specifically, examples of the Escherichia include *E. coli* DH1, M103, JA221, HB101, C600, XL-1 Blue, JM109 and TOP10. Examples of the Bacillus include *Bacillus subtilis* MI114 and 207-21. Examples of the yeast include *Saccharomvces cerevisiae* AH22, AH22R⁻, NA87-11A, DKD-5D, *Pichia pastoris* GS115 and KM71. The animal cells include monkey cell COS-7, Vero, Chinese hamster cell CHO, mouse L cell and human L cell. The insect cells include BmN4 and Sf9. However, the host cells are not limited thereto.

The PGRPs have the property of binding to peptidoglycans existing in cell walls. Accordingly, considering the influence to the host cells and the production efficiency of the PGRPs, of the above-mentioned host cells, ones having no peptidoglycans are preferably used in expressing the PGRPS.

Introduction of the expression vectors into the host cells (transformation including transduction) can be conducted by methods known in the art.

The transformation can be conducted, for example, by the method of Cohen et al. [*Proc. Natl. Acad. Sci. U.S.A.* 69, 2110 (1972)], the protoplast method [*Mol. Gene Genet.* 168, 111 (1979)] or the competent method [*J. Mol. Biol.* 56, 209, (1971)] for the bacteria (for example, *E. coli* and *Bacillus subtilis*), and for example, by the method of Hinnen et al. [*Proc. Natl. Acad. Sci. U.S.A.* 75, 1927 (1978)] or the lithium method [*J. Bacteriol.* 153, 163 (1983)] for *Saccharomyces cerevisiae*. In the case of the animal cells, the transformation can be performed, for example, by the method of Graham [*Virology* 52, 456 (1973)]. In the case of the insect cells, the transformation can be performed, for example, by the calcium phosphate precipitation method [Smith, G. E., et al., *J. Virol.*, 46, 584-593 (1983)]. However, the methods for transformation are not limited thereto.

The PGRP of the present invention can be produced by cultivating the transformant containing the expression vector prepared as described above in a nutrient medium.

The nutrient media preferably contain carbon sources, inorganic nitrogen sources or organic nitrogen sources necessary for growth of the host cells (transformants). Examples of the carbon sources include glucose, dextran, soluble starch and sucrose. Examples of the inorganic or organic nitrogen sources include ammonium salts, nitrates, amino acids, corn starch liquor, peptone, casein, meat extracts, soybean meal and potato extract solution. Further, the media may contain other nutrients such as inorganic salts (for example, calcium chloride, sodium dihydrogenphosphate and magnesium chloride), vitamins and antibiotics (for example, ampicillin and kanamycin) if necessary.

The cultivation is conducted according to methods known in the art. Cultivation conditions such as the temperature, the pH of media and the fermentation time are appropriately selected so as to give the maximum titer as peptidoglycan recognition activity of said polypeptides.

Specific media and cultivation conditions used according to the hosts are shown below, but are not limited thereto.

When the host cell is a bacterium, Actinomycetes, yeast or a mold, a liquid medium containing, for example, the above-mentioned nutrient(s) is suitably used. In that case, the pH is preferably 5 to 8.

When the host cell is *E. coli*, preferred examples of the media are LB medium, YT medium, SOB medium [*Molecular Cloning, A Laboratory Manual* 1, 82, Cold Spring Harbor Laboratory, (1982)] and M9 medium [Miller, *J. Exp. Mol. Genet.* page 431, Cold Spring Harbor Laboratory, New York (1972)]. In such cases, the cultivation can be carried out usually at 14° C. to 42° C., preferably at 28° C. to 39° C., for about 3 hours to about 24 hours with aeration and agitation if necessary.

When the host cell is Bacillus, the cultivation can be carried out usually at 14° C. to 42° C., preferably at 28° C. to 39° C., for about 3 hours to about 96 hours with aeration and agitation if necessary.

When the host cell is yeast, examples of the media include the medium developed by K. L. Bostian et al. [K. L. Bostian et al., *Proc. Natl. Acad. Sci. U.S.A.* 77, 4505 (1980)], which preferably has a pH of 5 to 8. The cultivation can be carried out usually at 14° C. to 42° C., preferably at 20° C. to 35° C., for about 12 hours to about 10 days with aeration and agitation if necessary.

When the host cell is an animal cell, examples of the media which can be used include MEM medium containing about 5 to 20% fetal calf serum [*Science* 122, 501 (1952)], DMEM medium [*Virology*, 8 396 (1959)], RPMI 1640 medium [*J. Am. Med. Assoc.* 199, 519 (1967)] and 199 medium [*Proc. Soc. Exp. Biol. Med.* 73, 1 (1950)]. The pH of the media is preferably about 6 to about 8, and the cultivation is carried out usually at about 30° C. to about 40° C., preferably at 34° C. to 38° C., for about 12 hours to about 72 hours with aeration and agitation if necessary.

When the host cell is an insect cell, examples of the media include Grace's medium [*Proc. Natl. Acad. Sci. U.S.A.* 82, 8404 (1985)] supplemented with fetal calf serum. The pH of the medium is preferably adjusted to about 5 to about 8. The cultivation is carried out usually at about 20° C. to about 40° C., preferably at 25° C. to 30° C. for about 12 hours to about 10 days with aeration and agitation if necessary.

Methods for producing the PGRPs by use of the transformants of the present invention also include a method of infecting insects such as silkworms with Baculovirus into which the DNAs of the present invention have been introduced breeding the insects, and recovering the PGRPs from their hemolymph.

Methods for obtaining the PGRPs of the present invention from broths obtained by the above-mentioned cultivation include, for example, the following methods.

That is, when the PGRPs of the present invention exist in culture solutions, the resulting cultures are subjected to filtration or centrifugation to obtain culture filtrates (supernatants). Then, the PGRPs are isolated and purified from the culture filtrates by conventional methods generally used for isolation and purification of natural or synthetic proteins.

The isolating and purifying methods include methods utilizing a difference in solubility such as salting-out and solvent precipitation, methods utilizing a difference in molecular weights, such as dialysis, ultrafiltration, gel filtration and sodium dodecylsulfonate-polyacrylamide gel electrophoresis (SDS-PAGE), methods utilizing specific affinity such as affinity chromatography, methods utilizing a difference in hydrophobicity such as reverse phase high performance liquid chromatography, and methods utilizing a difference in isoelectric point such as isoelectric point electrophoresis.

On the other hand, when the PGRPs of the present invention exist in periplasms or cytoplasms of the cultivated transformants, the cultures are subjected to conventional methods such as centrifugation to collect cells, which are suspended in appropriate buffer solutions. Then, cell walls and/or cell membranes are disrupted, for example, by ultrasonication, lysozyme, freeze-thawing or the like, followed by centrifugation or filtration to obtain crude fractions containing the polypeptides. Thereafter, said crude fractions can be isolated and purified according to the conventional methods shown above.

The present invention first elucidated the amino acid sequences of the PGRPs, and the nucleotide sequences coding for said amino acid sequences, thereby providing the method for producing the PGRPs by genetic engineering techniques and expression systems relating thereto. According to the present invention, the PGRPs previously difficult to be obtained became obtainable with ease, in large amounts and at high purity. The PGRPs of the present invention thus obtained have the following utilities:

(1) The detection of peptidoglycans is possible by observation of binding with labeled PGRPs, and the detection of bacteria is possible as well;

(2) Use of fixed PGRPs permits the concentration of peptidoglycans, and the concentration of bacteria as well, at high sensitivity without influence of various materials coexisting in samples such as salts; and (3) The peptidoglycans or the bacteria collected in (2) described above can be efficiently assayed with insect hemolymph reagents (Japanese Examined Patent Publication No. 7-114707).

According to the present invention, the following effects are achieved:

(1) It is possible to rapidly detect bacteria;

(2) Peptidoglycans in solids such as tissues can be detected;

(3) Bacteria in solids such as tissues can be detected at high sensitivity; and (4) In the method for assaying peptidoglycans by use of the insect hemolymph reagents, bacteria themselves are collected with filters. However, the peptidoglycans low in molecular weight can not be removed with filters. This is a problem in producing drugs to be introduced into blood flows, such as injections. On the other hand, according to the present invention, the peptidoglycans low in molecular weight can also be captured and concentrated. The present invention is therefore useful in producing injections free from impurities such as pyrogens.

Use of the PGRPs obtained by the method of the present invention to which appropriate labeling substances bind permits the detection of peptidoglycans in samples or cells at high sensitivity and high accuracy.

There is no particular limitation on the labeling substances used for labeling the PGRPs for such a purpose, as long as they can be used for detecting the peptidoglycans in samples or cells. Preferred examples thereof include enzymes such as alkaline phosphatase, β-galactosidase, peroxidase, microperoxidase, glucose oxidase, glucose 6-phosphate dehydrogenase, acetylcholin-esterase, malate dehydrogenase and luciferase used in enzyme immunoassays (EIAs), radioisotopes such as $^{99m}$Tc, $^{131}$I, $^{125}$I, $^{14}$C and $^3$H used in radio immunoassays (RIAs), fluorescent materials such as fluorescein, dansyl, fluorescamine, coumarin, naphthylamine and derivatives thereof used in fluorescent immunoassays (FIAs), luminous materials such as luciferin, isoluminol, luminol and bis(2,4,6-trifluorophenyl) oxalate, substances having absorption in an ultraviolet region such as phenol, naphthol, anthracene and derivatives thereof, and substances having the properties of spin labeling agents represented by compounds having oxyl groups such as 4-amino-2,2,6,6-tetramethylpiperidine-1-oxyl, 3-amino-2,2,5,5-tetramethylpyrrolidine-l-oxyl and 2,6-di-t-butyl-α-(3,5-di-t-butyl-4-oxo-2,5-cyclohexadiene-1-ylidene)-p-tolyloxyl.

Methods for binding the labeling substances as described above to the PGRPs (labeling the PGRPs with the labeling agents) include known methods for binding these labeling substances to proteins, which are generally used in the EIAs, the RIAs or the FIAs, for example, methods described in *Ikagaku Jikken Koza (Course of Experiments of Medical Chemistry)*, the first edition, vol. 8, edited by Yuichi Yamamura, Nakayama Shoten (1971); Akira Kawabu, *Iconographical Fluorescent Antibodies*, the first edition, Soft Science (1983); and Eiji Ishikawa, Tadashi Kawai, Kiyoshi Miyai, *Enzyme Immunoassavs*, the second edition, Igaku Shoin (1982), without exceptions.

Conventional methods utilizing the reaction of avidin (or streptavidin) and biotin may be used as the labeling methods.

In order to measure the amount of the peptidoglycans in samples or cells by use of the PGRPs according to the present invention to which appropriate labeling substances bind (hereinafter briefly referred to as labeled PGRPs), the labeling substances in complexes of the labeled PGRPs and the peptidoglycans are measured. The assays thereof are performed depending on properties detectable by some method according to respective prescribed methods. For example, in the case of enzyme activities, the assays are conducted based on the conventional EIAs such as methods described in Enzyme *Immunoassays, Proteins, Nucleic Acids and Enzymes*, separate volume No. 31, edited by Tsunehiro Kitagawa, Toshio Nanbara, Akio Tsuji and Eiji Ishikawa, pages 51–63, Kyoritsu Shuppan, published on Sep. 10, 1987. When the labeling substances are radioactive substances, any instrument suitably selected from measuring instruments such as an immersion type GM counter, a liquid scintillation counter, well type scintillation counter and a counter for HPLC depending on the kind and the intensity of radiation from the radioactive substances may be used for measurement according to the conventional RIAs [for example, refer to *Ikagaku Jikken Koza (Course of Experiments of Medical Chemistry)*, the first edition, vol. 8, edited by Yuichi Yamamura, Nakayama Shoten (1971)]. In the case of fluorescent properties, the assays are conducted based on the conventional FIAs using a measuring instrument such as a fluorometer, for example, methods described in Akira Kawabu, *Iconoaraphical Fluorescent Antibodies*, the first edition, Soft Science (1983). Further, in the case of luminous properties, the assays are conducted based on the conventional FIAs using a measuring instrument such as a photocounter, for example, methods described in *Enzyme Immunoassays, Proteins, Nucleic Acids and Enzymes*, separate volume No. 31, edited by Tsunehiro Kitagawa, Toshio Nanbara, Akio Tsuji and Eiji Ishikawa, pages 252–263, Kyoritsu Shuppan, published on Sep. 10, 1987. When the substances having absorption in an ultraviolet region are used, the assays are conducted based on the conventional methods using a measuring instrument such as a spectrophotometer. Furthermore, when the labeling substances are substances having spin properties, the assays are conducted based on the conventional methods using a measuring instrument such as an electron spin resonance instrument, for example, methods described in Enzyme *Immunoassays. Proteins. Nucleic Acids and Enzymes*, separate volume No. 31, edited by Tsunehiro Kitagawa, Toshio Nanbara, Akio Tsuji and Eiji Ishikawa, pages 264–271, Kyoritsu Shuppan, published on Sep. 10, 1987.

For example, use of the labeled PGRPs to which fluorescent labeling substances bind in combination with flow cytometry also makes it possible to fractionate peptidoglycan-containing cells and impurities (for example, peptidoglycan-free microorganisms such as molds and yeast, and peptidoglycan-free insoluble materials).

Use of the PGRPs obtained by the method of the present invention, which are fixed to appropriate carriers, also permits concentration of peptidoglycans in samples or peptidoglycan-containing cells, resulting in a great increase in detection sensitivity of the peptidoglycans in samples or the peptidoglycan-containing cells.

There is no particular limitation on the carriers used for fixation of the PGRPs, as long as they are ones usually employed in the field of affinity chromatography. Preferred examples thereof include cellulose carriers such as Cellulofine (CHISSO CORP.), agarose carriers such as Sepharose (trade name, Pharmacia) and Biogel A (trade name, Bio RAD), dextran carriers such as Sephadex (trade name, Pharmacia) and Sephacryl (trade name, Pharmacia), polyacrylamide carriers such as Enzafix P (Wako Pure Chemical Industries) and Biogel P (Bio RAD), porous glass and synthetic polymer carriers such as polystyrene and polypropylene.

There is no particular limitation on the shapes of these carriers, as long as they are usually employed in this field. Examples thereof include sheet (film), tube, bead, disk piece, plate and fine grain shapes.

There is no particular limitation on methods for fixing the PGRPs to such carriers, as long as they are methods usually employed in the field of affinity chromatography to bind the carriers as described above to proteins.

For example, when the carriers contain saccharides, more specifically, in the case of cellulose carriers, agarose carriers and dextran carriers, they are activated, and then reacted with the PGRPs, thereby easily obtaining PGRP-fixed carriers.

As methods for activating such carriers, all the activating methods of saccharide compounds usually widely known in this field can be used. Specific examples thereof include a method of activating hydroxyl groups with cyanuric chloride [for example, *J. Solid-Phase Biochem.* 4, 2128 (1976)], a method of activating aldehyde groups by oxidation with metaperiodic acid [for example, *Proc. Natl. Acad. Sci. U.S.A.* 73, 2128 (1976)], a method of activating hydroxyl groups with bromocyanogen [for example, *Nature* 214, 1302 (1967)] and a method of activating hydroxyl groups with epichlorohydrin [for example, *J. Chromatog.* 51, 479 (1970)].

The carriers activated by the methods as described above are brought into contact with the PGRPs, thereby easily covalently binding to them. Before the reaction with the PGRPs, compounds which can act as ligands for binding the carriers to the PGRPs may be further allowed to bind to these carriers, followed by the reaction with the enzymes.

Further, when the carriers as described above have reactive groups, the PGRP-fixed carriers can also be obtained by the following methods.

Namely, for example, when reactive groups of the carriers and PGRP reactive groups are amino groups and carboxyl groups, examples of the methods include the carbodiimide method [for example, *J. Biol. Chem.* 245, 3059 (1970)], the activated ester method [for example, *Cancer Biochem.* 7, 175 (1984)], the acid anhydride method [for example, *J. Biol. Chem.* 237, 1825 (1962)], the azide method [for example, *Eur. J. Biochem.* 25, 129 (1972)], the carbonyl chloride method [for example, *Angew. Chem.* 67, 661 (1955)], the isocyanate method [for example, *Nature* 210, 367 (1966)], the Woodward reagent method [for example, *Biochim. Biophys. Acta* 178, 626 (1969)] and the Ugi reaction [for example, *Anqew. Chem.* 74, 9 (1962)]. When both the reactive groups of the carriers and the PGRP reactive groups are amino acid groups, examples of the methods include the glutaraldehyde method [for example, *Experientia* 28, 958 (1973)] and the alkylation method [for example, *Biochim. Biophys. Acta* 198, 276 (1970)]. When the reactive groups of the carriers and the PGRP reactive groups are hydroxyl groups and amino groups, examples of the methods include the alkylation method [for example, *Biochim. Biophys. Acta* 198, 276 (1970)].

Further, when the PGRPs are fixed to the carriers, the avidin-biotin reaction may be utilized.

When nucleotides, amino acids and so on are indicated by abbreviations in the specification and drawing of this invention, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
   A: Adenine
   T: Thymine
   G: Guanine
   C: Cytosine
RNA : Ribonucleic acid
mRNA: Messenger ribonucleic acid
   Gly or G: Glycine
   Ala or A: Alanine
   Val or V: Valine
   Leu or L: Leucine
   Ile or I: Isoleucine
   Ser or S: Serine
   Thr or T: Threonine
   Cys or C: Cysteine
   Met or M: Methionine
   Glu or E: Glutamic acid
   Asp or D: Aspartic acid
   Lys or K: Lysine
   Arg or R: Arginine
   His or H: Histidine
   Phe or F: Phenylalanine
   Tyr or Y: Tyrosine
   Trp or W: Tryptophan
   Pro or P: Proline
   Asn or N: Asparagine
   Gin or Q: Glutamine Although plasmids, enzymes such as restriction enzymes and other materials used in Reference Example and Examples shown below are described in the following Reference Example and Examples, commercial products can also be used. They can also be used according to the conventional methods. Operation methods in DNA cloning, transformation of host cells, cultivation of transformants, collection of PGRPs from the resulting cultures and purification thereof are methods well known in the art or methods which can be known from the literature.

Reference Example and Examples are shown below, but the present invention is not construed as being limited by descriptions given therein.

Reference Example

Materials and Methods Used in Experiments
Purification of PGRP

Silkworm larvae on the 5th or 6th day of the fifth instar were bled by cutting abdominal legs with scissors. Hemolymph was collected, and immediately mixed with saturated ammonium sulfate, pH 6.5, with vigorous stirring. Hemolymph (250 ml) obtained from about 400 silkworm larvae was collected into 400 ml of saturated ammonium sulfate and stored at 4° C. until use. Subsequent procedures were performed at a temperature of 0° C. to The fraction having the highest PGRP activity was used as a PGRP sample for analysis.

The PGRP sample was passed through a reversed phase cyanopropyl-derived silica high performance liquid chromatography column (4.6 mm in inner diameter×250 mm, pore size: 300 Å) in the following manner. That is, 0.5 ml of a PGRP solution (10 mM Tris-HCl buffer, pH 7.5, containing about 40 μg/ml of protein and 0.1 M NaCl) was applied to the above-mentioned column, and then eluted with a gradient of $CH_3CN$ from 30% to 70% in 0.1% $CF_3COOHaH_2O$ at a flow rate of 0.4 ml/minute. It took 50 minutes to terminate this gradient. The only one protein peak appeared at 29.69 minutes from the initiation of the gradient elution. Proteins contained in this peak were pooled and lyophilized (protein content: 283 μg).

Sequencing of N-Terminal Amino Acid of PGRP The PGRP purified on the reversed phase cyanopropyl-derived silica HPLC column was analyzed for the sequence of 20 amino acids from the N-terminal by automated Edman degradation with a protein sequencer (Model 477A, Applied Biosystems).

As a result, the N-terminal 20 amino acids of the PGRP were analyzed as follow:

H-Asp-X-Asp-Val-Val-Ser-Lys-Lys-Gln-Trp-Asp-Gly-Leu-Ile-Pro-Val-His-Val-Ser- Tyr- (SEQ ID NO: 13)

Assay of Peptidoglycan Recognition Activity

Peptidoglycan recognition activity was measured in the following manner based on the description of *J. Bio. Chem.*

271 (23), 13854–13860 (1992). A sample to be measured for peptidoglycan recognition activity was continuously diluted, and 10 µl of each dilution was added to a mixture of 5 µl of 80 mM $CaCl_2$, 50 µl of plasma-PG and 5 µl of the peptidoglycan (1 mg/ml of peptidoglycan in distilled deionized water, prepared by the method of Yoshida et al., *Biochem. Biophvs. Res. Commun.* 141, 1177–1184), followed by incubation at 25° C. for 120 minutes. At the end of the incubation, phenol oxidase. activity. of the reaction mixture was measured by spectrophotometric analysis. In order to avoid the possibility that the observed activation of phenol oxidase was independent of the peptidoglycan action, phenol oxidase activity of the peptidoglycan-free reaction mixture was always checked after the incubation.

The greatest dilution giving a phenol oxidase activity of more than 30 units to the reaction mixture by the incubation for 120 minutes was, determined, and this dilution factor was used as a tentative measure for quantifying the amount of peptidoglycan recognition activity. This factor is expressed in terms of the number of units of peptidoglycan recognition activity/ml of sample solution.

EXAMPLE 1

Sequencing of Nucleotide Sequence of DNA Coding for PGRP and Amino Acid Sequence of PGRP (1) Preparation of Silkworm Fat Body cDNA Library From 5 silkworm larvae (the 4th day after ecdysis) of the fifth instar, 25 ml of fat body was collected, and total RNA (about 800 µg) was prepared by use of ISOGEN (Nippon Gene), a reagent for preparing total RNA. At this time, the band of ribosome 28S RNA was confirmed by agarose electrophoresis, and no decomposition of RNA was also confirmed. The total RNA was purified by use of an mRNA purification kit (Pharmacia) to obtain mRNA (about 20 µg), and synthesis of cDNA were conducted by use of a ZAP CDNA synthesis kit (Strata Gene) and in vitro packaging of CDNA were conducted As a result, a cDNA library having a plaque forming unit (PFU) of $1 \times 10^7$ was obtained.

(2) Preparation of Probe for Screening

The purified PGRP (about 500 pmol) obtained in Reference Example was digested with trypsin (PGRP: trypsin= 50:1, 37° C., 16 hours, 0.1 M Tris-HCl, pH 8.0), and peptide mapping was performed on an ODS column, thus obtaining the following sequences by amino acid sequence analysis (Shimazu PSQ10):

KKQWDG . . . (SEQ ID NO: 9)

WPEWLE . . . (SEQ ID NO: 10)

Based on these sequences, the following primers for PCR were synthesized:

```
              G  G G     T          (SEQ ID NO: 11)
5' AAGAATTCAA AACA TGGGA GG 3'
              A  A A     C

G       G             (SEQ ID NO: 12)
              A A   C A
5' AAGAATTCTCTAGCCATTCTGGCCA 3'
EcoRI site  C         C
```

Using the above-mentioned library as a template, the PCR was conducted 40 cycles by a unit of 94° C. (1 second),–60° C. (2 minutes) and –72° C. (3 minutes). 4° C., and centrifugation was carried out at 12,000×g for 20 minutes unless otherwise specified. The product was centrifuged, and the precipitate was suspended in 390 ml of 0.2 M potassium phosphate buffer, pH 6.5, containing 1 mM EDTA, 1 mM 1,10-phenanthroline, 1 mM phenylmethanesulfonyl fluoride, 5 mM phenylthiourea and 1% ethanol. The suspension was stirred for 2 hours, followed by centrifugation at 4,800×g for 20 minutes. Ammonium sulfate was added to the supernatant (69 g/500 ml of supernatant), and the resulting mixture was stirred for 2 hours. Then, the precipitate was collected by centrifugation, and dissolved in 100 ml of 0.1 M potassium phosphate buffer, pH 6.5, containing the above-mentioned additives. The solution was dialyzed against 0.2M potassium phosphate buffer mentioned above (1.9 liters) for 30 hours, and further dialyzed against two changes of 0.1 M potassium phosphate buffer, pH 6.5.

The dialyzed solution was applied at a flow rate of 20 ml/hour to a peptidoglycan-Sepharose 4B column (5 cm×2.5 cm in inner diameter) prepared according to the method of Yoshida et al. with the exception that lysozyme-digested peptidoglycan was used without fractionation by column chromatography on Sephadex G-5. This column was continuously eluted at 20 ml/hour with the following eluants: 50 ml of 0.1 M potassium phosphate, pH 6.5; a linear gradient of KCl from 0 to 2 M in a total volume of 120 ml of 0.1 M potassium phosphate buffer, pH 6.5; and 60 ml of 5 mM MES, pH 5.5, containing 2 M KCl. The final elution was carried out at a flow rate of 220 ml/hour by use of 150 ml of 5 mM acetate buffer, pH 4.5, containing 2 M KCl. Fractions (30 ml) were collected into containers each containing 1.2 ml of 0.5 M PIPES, pH 7.0. All the fractions were dialyzed separately against 3 liters of 10 mM potassium phosphate buffer, pH 6.5, for 18 hours with a change of buffer. The following column chromatography was conducted at room temperature on a fast protein, liquid chromatography system (FPLC: Pharmacia LKB Biotechnology Inc.). The active fractions obtained in the previous procedure were applied at a flow rate of 1 ml/minute to a hydroxyapatite column (100 mm×7.8 mm in inner diameter, Koken Ltd., Tokyo) for high pressure liquid chromatography, previously equilibrated with 10 mM potassium phosphate, pH 6.5, and washed with 10 ml of the same buffer. The adsorbed proteins were eluted at a flow rate of 1.0 ml/minute with two consecutive linear gradients of potassium phosphate buffer, pH 6.5, from 10 mM to 144 mM and from 144 mM to 1 M with concentration incremental rates of 2.48 and 93 mM/minute, respectively. The volume of one fraction was 1.5 ml. Fractions eluted between 190 minutes and 198 minutes from the application of the phosphate gradient were pooled, and subjected to salting out overnight against 2 liters of 10 mM triethanolamine-HCl buffer, pH 7.5. The dialyzed fractions were applied to a Mono Q column (HR 5/5) (Pharmacia LKB Biotechnology Inc.) equilibrated with the same buffer as that used for salting out. The adsorbed proteins were eluted with a linear salt gradient in the same buffer. The flow rate was maintained at 1 ml/minute, and 1.5-ml fractions were collected.

As a result, a band of about 0.5 kbp was detected. This band was subcloned into the EcoRI site of pBluescript II SK(+), and DNA sequence analysis was carried out. It was confirmed that the DNA sequence agreed with a DNA sequence recognizing the PGRP-derived amino acid sequence. After cleavage with EcoRI, 0.5-Kbp DNA was extracted to use it as a probe for screening.

(3) Screening

Thirty plates (82 mm in diameter) having $1 \times 10^4$ plaques/ plate were hybridized with the above-mentioned probe for screening (42° C., 16 hours, 50% formamide), thereby obtaining 8 positive clones. The clones were subcloned into pBluescript II SK(–) by use of helper phage, and DNA sequence analysis (ABI 377) was carried out. As a result, a PGRP cDNA clone having a full length of 0.75 Kbp shown in FIG. 1 (SEQ ID NO: 7) was obtained.

The homology between the nucleotide sequence of this clone and the nucleotide sequence coding for the N-terminal 20 amino acids of the PGRP in silkworm hemolymph was studied, resulting in the decision that the nucleotide sequence of cDNA coding for the PGRP starts from the 100th nucleotide from the 5'-terminal.

As a result, a PGRP-related amino acid sequence composed of 196 amino acid residues having ATG starting from the 31st nucleotide from the 5'-terminus as a translation initiation sequence, and the 621st nucleotide as a translation termination sequence was elucidated from the 753-bp clone.

The results of analysis of the N-terminal amino acid sequence of the PGRP in silkworm hemolymph bring about the decision that, of the amino acid residues from the 1st to the 196th, the amino acid residues from the 1st methionine to the 23rd aspartic acid form a pro portion and the amino acid residues from the 24th asparagine to the 196th aspartic acid form a mature PGRP (SEQ ID NO: 1).

EXAMPLE 2

Expression of PGRP Protein

The clone containing DNA coding for the PGRP having the full length obtained in Example 1 was cleaved with EcoRI and XhoI, and a 0.75-Kbp DNA was extracted. Then, an EcoRI linker was added to the XhoI-cleaved end of the resulting DNA fragment. This was cloned into the EcoRI site of expression vector pHIL-D2, and yeast (*Pichia Pastoris*) was transformed therewith. The resulting transformant was cultivated in YPD medium until the $OD_{600}$ reached 2 to 6, and the transformant was collected by centrifugation. Then, the transformant was resuspended in SOS medium containing 0.5% (final concentration) methanol so as to give an $OD_{600}$ of 1.0, and cultivated with shaking at 30° C. for 96 hours. The culture solution was centrifuged to collect a precipitate, which was resuspended in PBS. This was centrifuged again to obtain a precipitate, which was suspended in stabilizing buffer A [1 M sorbitol, 10 mM $MgCl_2$, 2 mM dithiothreitol (DTT), 50 mM potassium phosphate (pH 7.8), 100 μg/ml phenylmethyl-sulfonyl fluoride (PMSF)], followed by heating at 30° C. for 10 minutes. After centrifugation, the resulting precipitate was resuspended in stabilizing buffer B [1 M sorbitol, 10 mM $MgCl_2$, 2 mM DTT, 25 mM potassium phosphate (pH 7.8), 25 mM sodium succinate, 100 μg/ml PMSF], followed by heating at 30° C. for 2 minutes. Then, a 0.25-fold amount of 10 mg/ml zymolase was added thereto, followed by treatment at 30° C. for 30 minutes. After treatment, a precipitate obtained by further centrifugation was suspended in lysis buffer [50 mM HEPES (pH 7.0), 1% NP-40, 1 μl/ml aprotinin, 100 μg/ml PMSF], and the resulting suspension was allowed to stand at 0° C. for 30 minutes, followed by collection of a supernatant by centrifugation.

Peptidoglycan recognition activity in the resulting supernatant was measured based on the method described in *J. Bio. Chem.* 271 (23), 13885 (1992) (also refer to Reference Example described above).

As a result, peptidoglycan recognition activity was recognized in the resulting supernatant to confirm expression of the PGRP.

What is claimed is:

1. A method for detecting a peptidoglycan and/or bacteria in a sample which comprises, contacting the sample with a recombinant protein having the amino acid sequence of SEQ ID NO: 1, which is labeled by a labeling substance to give a complex of the labeled recombinant protein and peptidoglycan, and measuring the labeling substance in the complex to detect the peptidoglycan and/or bacteria.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 173 amino acids
      (B) TYPE: amino acid
      (D) TOPOLOGY: linear (ii) MOLECULE TYPE: protein (xi) SEQUENCE DESCRIPTION: SEQ ID NO:1:

```
Asp Cys Asp Val Val Ser Lys Lys Gln Trp Asp Gly Leu Ile Pro Val
 1               5                  10                  15

His Val Ser Tyr Leu Ala Arg Pro Val Ser Leu Val Ile Val Gln His
                20                  25                  30

Thr Val Thr Pro Phe Cys Arg Thr Asp Ala Gly Cys Glu Glu Leu Val
            35                  40                  45

Arg Asn Ile Gln Thr Asn His Met Glu Ala Leu Gln Tyr Trp Asp Ile
        50                  55                  60

Gly Pro Ser Phe Leu Val Gly Gly Asn Gly Lys Val Tyr Glu Gly Ser
65                  70                  75                  80

Gly Trp Leu His Val Gly Ala His Thr Tyr Gly Tyr Asn Ser Arg Ser
                85                  90                  95

Ile Gly Val Ala Phe Ile Gly Asn Phe Asn Thr Asp Glu Pro Ser Gly
            100                 105                 110

Ala Met Leu Glu Ala Leu Arg Ser Leu Leu Arg Cys Gly Val Glu Arg
```

```
              115                 120                 125
Gly His Leu Ala Gly Asp Tyr Arg Val Val Ala His Arg Gln Leu Ile
    130                 135                 140

Ala Ser Glu Ser Pro Gly Arg Lys Leu Tyr Asn Gln Ile Arg Arg Trp
145                 150                 155                 160

Pro Glu Trp Leu Glu Asn Val Asp Ser Ile Lys Asn Ala
                165                 170
```

(2) INFORMATION FOR SEQ ID NO:2:

(i) SEQUENCE CHARACTERISTICS:
        (A) LENGTH: 196 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Arg Leu His Ser Ala Val Val Leu Ala Leu Ala Leu Ser Ser
1               5                   10                  15

Leu Leu Thr Glu Ile Ala Ala Asp Cys Asp Val Val Ser Lys Lys Gln
            20                  25                  30

Trp Asp Gly Leu Ile Pro Val His Val Ser Tyr Leu Ala Arg Pro Val
        35                  40                  45

Ser Leu Val Ile Val Gln His Thr Val Thr Pro Phe Cys Arg Thr Asp
    50                  55                  60

Ala Gly Cys Glu Glu Leu Val Arg Asn Ile Gln Thr Asn His Met Glu
65                  70                  75                  80

Ala Leu Gln Tyr Trp Asp Ile Gly Pro Ser Phe Leu Val Gly Gly Asn
                85                  90                  95

Gly Lys Val Tyr Glu Gly Ser Gly Trp Leu His Val Gly Ala His Thr
            100                 105                 110

Tyr Gly Tyr Asn Ser Arg Ser Ile Gly Val Ala Phe Ile Gly Asn Phe
        115                 120                 125

Asn Thr Asp Glu Pro Ser Gly Ala Met Leu Glu Ala Leu Arg Ser Leu
    130                 135                 140

Leu Arg Cys Gly Val Glu Arg Gly His Leu Ala Gly Asp Tyr Arg Val
145                 150                 155                 160

Val Ala His Arg Gln Leu Ile Ala Ser Glu Ser Pro Gly Arg Lys Leu
                165                 170                 175

Tyr Asn Gln Ile Arg Arg Trp Pro Glu Trp Leu Glu Asn Val Asp Ser
            180                 185                 190

Ile Lys Asn Ala
        195
```

(2) INFORMATION FOR SEQ ID NO:3:

(i) SEQUENCE CHARACTERISTICS:
        (A) LENGTH: 522 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..522

(xi) SEQUENCE DESCRIPTION: SEQ ID NO:3:

```
GAT TGC GAC GTC GTC AGT AAA AAG CAA TGG GAC GGT TTG ATC CCG GTG        48
Asp Cys Asp Val Val Ser Lys Lys Gln Trp Asp Gly Leu Ile Pro Val
 1               5                  10                  15

CAC GTG TCG TAC CTG GCG CGG CCC GTG AGC CTC GTC ATC GTC CAG CAC        96
His Val Ser Tyr Leu Ala Arg Pro Val Ser Leu Val Ile Val Gln His
                 20                  25                  30

ACA GTC ACA CCC TTC TGC AGG ACG GAC GCT GGC TGC GAG GAG CTC GTG       144
Thr Val Thr Pro Phe Cys Arg Thr Asp Ala Gly Cys Glu Glu Leu Val
             35                  40                  45

CGG AAT ATC CAG ACC AAC CAC ATG GAG GCC TTG CAA TAC TGG GAC ATC       192
Arg Asn Ile Gln Thr Asn His Met Glu Ala Leu Gln Tyr Trp Asp Ile
         50                  55                  60

GGA CCC TCG TTC CTG GTG GGA GGT AAC GGC AAG GTG TAC GAG GGC TCC       240
Gly Pro Ser Phe Leu Val Gly Gly Asn Gly Lys Val Tyr Glu Gly Ser
 65                  70                  75                  80

GGC TGG CTG CAC GTC GGC GCG CAC ACC TAC GGG TAC AAC TCG AGG TCC       288
Gly Trp Leu His Val Gly Ala His Thr Tyr Gly Tyr Asn Ser Arg Ser
                 85                  90                  95

ATC GGA GTC GCA TTC ATC GGC AAC TTC AAC ACG GAC GAG CCG AGC GGC       336
Ile Gly Val Ala Phe Ile Gly Asn Phe Asn Thr Asp Glu Pro Ser Gly
             100                 105                 110

GCG ATG CTG GAG GCG CTG CGG TCG CTG CTG CGC TGC GGC GTG GAG CGC       384
Ala Met Leu Glu Ala Leu Arg Ser Leu Leu Arg Cys Gly Val Glu Arg
         115                 120                 125

GGC CAC CTC GCG GGG GAC TAC CGC GTC GTG GCG CAC CGA CAG CTC ATT       432
Gly His Leu Ala Gly Asp Tyr Arg Val Val Ala His Arg Gln Leu Ile
 130                 135                 140

GCC TCT GAG AGC CCC GGC CGG AAG CTC TAC AAC CAG ATA CGA CGC TGG       480
Ala Ser Glu Ser Pro Gly Arg Lys Leu Tyr Asn Gln Ile Arg Arg Trp
145                 150                 155                 160

CCT GAG TGG CTG GAG AAC GTG GAC TCC ATC AAG AAC GCG TAA               522
Pro Glu Trp Leu Glu Asn Val Asp Ser Ile Lys Asn Ala
                 165                 170

(2) INFORMATION FOR SEQ ID NO:4:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:4:

Asp Cys Asp Val Val Ser Lys Lys Gln Trp Asp Gly Leu Ile Pro Val
 1               5                  10                  15

His Val Ser Tyr Leu Ala Arg Pro Val Ser Leu Val Ile Val Gln His
                 20                  25                  30

Thr Val Thr Pro Phe Cys Arg Thr Asp Ala Gly Cys Glu Glu Leu Val
             35                  40                  45

Arg Asn Ile Gln Thr Asn His Met Glu Ala Leu Gln Tyr Trp Asp Ile
         50                  55                  60

Gly Pro Ser Phe Leu Val Gly Gly Asn Gly Lys Val Tyr Glu Gly Ser
 65                  70                  75                  80

Gly Trp Leu His Val Gly Ala His Thr Tyr Gly Tyr Asn Ser Arg Ser
                 85                  90                  95

Ile Gly Val Ala Phe Ile Gly Asn Phe Asn Thr Asp Glu Pro Ser Gly
             100                 105                 110

Ala Met Leu Glu Ala Leu Arg Ser Leu Leu Arg Cys Gly Val Glu Arg
         115                 120                 125
```

```
Gly His Leu Ala Gly Asp Tyr Arg Val Val Ala His Arg Gln Leu Ile
    130                 135                 140

Ala Ser Glu Ser Pro Gly Arg Lys Leu Tyr Asn Gln Ile Arg Arg Trp
145                 150                 155                 160

Pro Glu Trp Leu Glu Asn Val Asp Ser Ile Lys Asn Ala
                165                 170

(2) INFORMATION FOR SEQ ID NO:5:

(i) SEQUENCE CHARACTERISTICS:
        (A) LENGTH: 591 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..591

(xi) SEQUENCE DESCRIPTION: SEQ ID NO:5:

ATG GCC CGC CTC CAC TCG GCA GTT GTA CTC GCG CTC GCT CTC AGC TCG        48
Met Ala Arg Leu His Ser Ala Val Val Leu Ala Leu Ala Leu Ser Ser
  1               5                  10                  15

CTT CTC ACA GAA ATA GCA GCC GAT TGC GAC GTC GTC AGT AAA AAG CAA        96
Leu Leu Thr Glu Ile Ala Ala Asp Cys Asp Val Val Ser Lys Lys Gln
             20                  25                  30

TGG GAC GGT TTG ATC CCG GTG CAC GTG TCG TAC CTG GCG CGG CCC GTG       144
Trp Asp Gly Leu Ile Pro Val His Val Ser Tyr Leu Ala Arg Pro Val
         35                  40                  45

AGC CTC GTC ATC GTC CAG CAC ACA GTC ACA CCC TTC TGC AGG ACG GAC       192
Ser Leu Val Ile Val Gln His Thr Val Thr Pro Phe Cys Arg Thr Asp
     50                  55                  60

GCT GGC TGC GAG GAG CTC GTG CGG AAT ATC CAG ACC AAC CAC ATG GAG       240
Ala Gly Cys Glu Glu Leu Val Arg Asn Ile Gln Thr Asn His Met Glu
 65                  70                  75                  80

GCC TTG CAA TAC TGG GAC ATC GGA CCC TCG TTC CTG GTG GGA GGT AAC       288
Ala Leu Gln Tyr Trp Asp Ile Gly Pro Ser Phe Leu Val Gly Gly Asn
                 85                  90                  95

GGC AAG GTG TAC GAG GGC TCC GGC TGG CTG CAC GTC GGC GCG CAC ACC       336
Gly Lys Val Tyr Glu Gly Ser Gly Trp Leu His Val Gly Ala His Thr
            100                 105                 110

TAC GGG TAC AAC TCG AGG TCC ATC GGA GTC GCA TTC ATC GGC AAC TTC       384
Tyr Gly Tyr Asn Ser Arg Ser Ile Gly Val Ala Phe Ile Gly Asn Phe
        115                 120                 125

AAC ACG GAC GAG CCG AGC GGC GCG ATG CTG GAG GCG CTG CGG TCG CTG       432
Asn Thr Asp Glu Pro Ser Gly Ala Met Leu Glu Ala Leu Arg Ser Leu
    130                 135                 140

CTG CGC TGC GGC GTG GAG CGC GGC CAC CTC GCG GGG GAC TAC CGC GTC       480
Leu Arg Cys Gly Val Glu Arg Gly His Leu Ala Gly Asp Tyr Arg Val
145                 150                 155                 160

GTG GCG CAC CGA CAG CTC ATT GCC TCT GAG AGC CCC GGC CGG AAG CTC       528
Val Ala His Arg Gln Leu Ile Ala Ser Glu Ser Pro Gly Arg Lys Leu
                165                 170                 175

TAC AAC CAG ATA CGA CGC TGG CCT GAG TGG CTG GAG AAC GTG GAC TCC       576
Tyr Asn Gln Ile Arg Arg Trp Pro Glu Trp Leu Glu Asn Val Asp Ser
            180                 185                 190

ATC AAG AAC GCG TAA                                                   591
Ile Lys Asn Ala
            195
```

(2) INFORMATION FOR SEQ ID NO:6:

(i) SEQUENCE CHARACTERISTICS:
        (A) LENGTH: 196 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Arg Leu His Ser Ala Val Val Leu Ala Leu Ala Leu Ser Ser
 1               5                  10                  15

Leu Leu Thr Glu Ile Ala Ala Asp Cys Asp Val Val Ser Lys Lys Gln
            20                  25                  30

Trp Asp Gly Leu Ile Pro Val His Val Ser Tyr Leu Ala Arg Pro Val
        35                  40                  45

Ser Leu Val Ile Val Gln His Thr Val Thr Pro Phe Cys Arg Thr Asp
    50                  55                  60

Ala Gly Cys Glu Glu Leu Val Arg Asn Ile Gln Thr Asn His Met Glu
65                  70                  75                  80

Ala Leu Gln Tyr Trp Asp Ile Gly Pro Ser Phe Leu Val Gly Gly Asn
                85                  90                  95

Gly Lys Val Tyr Glu Gly Ser Gly Trp Leu His Val Gly Ala His Thr
            100                 105                 110

Tyr Gly Tyr Asn Ser Arg Ser Ile Gly Val Ala Phe Ile Gly Asn Phe
        115                 120                 125

Asn Thr Asp Glu Pro Ser Gly Ala Met Leu Glu Ala Leu Arg Ser Leu
130                 135                 140

Leu Arg Cys Gly Val Glu Arg Gly His Leu Ala Gly Asp Tyr Arg Val
145                 150                 155                 160

Val Ala His Arg Gln Leu Ile Ala Ser Glu Ser Pro Gly Arg Lys Leu
                165                 170                 175

Tyr Asn Gln Ile Arg Arg Trp Pro Glu Trp Leu Glu Asn Val Asp Ser
            180                 185                 190

Ile Lys Asn Ala
        195
```

(2) INFORMATION FOR SEQ ID NO:7:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 31..621

(xi) SEQUENCE DESCRIPTION: SEQ ID NO:7:

```
CTGACGTGCT GGCACGCGCC GCTCCTCGAC ATG GCC CGC CTC CAC TCG GCA GTT        54
                                Met Ala Arg Leu His Ser Ala Val
                                 1               5

GTA CTC GCG CTC GCT CTC AGC TCG CTT CTC ACA GAA ATA GCA GCC GAT        102
Val Leu Ala Leu Ala Leu Ser Ser Leu Leu Thr Glu Ile Ala Ala Asp
         10                  15                  20

TGC GAC GTC GTC AGT AAA AAG CAA TGG GAC GGT TTG ATC CCG GTG CAC        150
Cys Asp Val Val Ser Lys Lys Gln Trp Asp Gly Leu Ile Pro Val His
 25                  30                  35                  40
```

```
GTG TCG TAC CTG GCG CGG CCC GTG AGC CTC GTC ATC GTC CAG CAC ACA    198
Val Ser Tyr Leu Ala Arg Pro Val Ser Leu Val Ile Val Gln His Thr
             45                  50                  55

GTC ACA CCC TTC TGC AGG ACG GAC GCT GGC TGC GAG GAG CTC GTG CGG    246
Val Thr Pro Phe Cys Arg Thr Asp Ala Gly Cys Glu Glu Leu Val Arg
             60                  65                  70

AAT ATC CAG ACC AAC CAC ATG GAG GCC TTG CAA TAC TGG GAC ATC GGA    294
Asn Ile Gln Thr Asn His Met Glu Ala Leu Gln Tyr Trp Asp Ile Gly
         75                  80                  85

CCC TCG TTC CTG GTG GGA GGT AAC GGC AAG GTG TAC GAG GGC TCC GGC    342
Pro Ser Phe Leu Val Gly Gly Asn Gly Lys Val Tyr Glu Gly Ser Gly
         90                  95                 100

TGG CTG CAC GTC GGC GCG CAC ACC TAC GGG TAC AAC TCG AGG TCC ATC    390
Trp Leu His Val Gly Ala His Thr Tyr Gly Tyr Asn Ser Arg Ser Ile
105                 110                 115                 120

GGA GTC GCA TTC ATC GGC AAC TTC AAC ACG GAC GAG CCG AGC GGC GCG    438
Gly Val Ala Phe Ile Gly Asn Phe Asn Thr Asp Glu Pro Ser Gly Ala
                125                 130                 135

ATG CTG GAG GCG CTG CGG TCG CTG CTG CGC TGC GGC GTG GAG CGC GGC    486
Met Leu Glu Ala Leu Arg Ser Leu Leu Arg Cys Gly Val Glu Arg Gly
            140                 145                 150

CAC CTC GCG GGG GAC TAC CGC GTC GTG GCG CAC CGA CAG CTC ATT GCC    534
His Leu Ala Gly Asp Tyr Arg Val Val Ala His Arg Gln Leu Ile Ala
            155                 160                 165

TCT GAG AGC CCC GGC CGG AAG CTC TAC AAC CAG ATA CGA CGC TGG CCT    582
Ser Glu Ser Pro Gly Arg Lys Leu Tyr Asn Gln Ile Arg Arg Trp Pro
        170                 175                 180

GAG TGG CTG GAG AAC GTG GAC TCC ATC AAG AAC GCG TAACATTATC         628
Glu Trp Leu Glu Asn Val Asp Ser Ile Lys Asn Ala
185                 190                 195

ACAGCGTATC GCATAGCGCC GTTCTTGTTG TGTTCAGATC TTGGACAAGT GTCAACTCAT  688

ATAGTATTTA CGCGTAATAT AATTTAAACT ACTTATAAAT TAAAATTAAA AAAAAAAAAA  748

AAAAA                                                             753

(2) INFORMATION FOR SEQ ID NO:8:

(i) SEQUENCE CHARACTERISTICS:
        (A) LENGTH: 196 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Arg Leu His Ser Ala Val Val Leu Ala Leu Ala Leu Ser Ser
  1               5                  10                  15

Leu Leu Thr Glu Ile Ala Ala Asp Cys Asp Val Ser Lys Lys Gln
             20                  25                  30

Trp Asp Gly Leu Ile Pro Val His Val Ser Tyr Leu Ala Arg Pro Val
             35                  40                  45

Ser Leu Val Ile Val Gln His Thr Val Thr Pro Phe Cys Arg Thr Asp
         50                  55                  60

Ala Gly Cys Glu Glu Leu Val Arg Asn Ile Gln Thr Asn His Met Glu
 65                  70                  75                  80

Ala Leu Gln Tyr Trp Asp Ile Gly Pro Ser Phe Leu Val Gly Gly Asn
                 85                  90                  95

Gly Lys Val Tyr Glu Gly Ser Gly Trp Leu His Val Gly Ala His Thr
                100                 105                 110
```

Tyr Gly Tyr Asn Ser Arg Ser Ile Gly Val Ala Phe Ile Gly Asn Phe
            115                 120                 125

Asn Thr Asp Glu Pro Ser Gly Ala Met Leu Glu Ala Leu Arg Ser Leu
        130                 135                 140

Leu Arg Cys Gly Val Glu Arg Gly His Leu Ala Gly Asp Tyr Arg Val
145                 150                 155                 160

Val Ala His Arg Gln Leu Ile Ala Ser Glu Ser Pro Gly Arg Lys Leu
                165                 170                 175

Tyr Asn Gln Ile Arg Arg Trp Pro Glu Trp Leu Glu Asn Val Asp Ser
            180                 185                 190

Ile Lys Asn Ala
        195

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Lys Lys Gln Trp Asp Gly
1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Trp Pro Glu Trp Leu Glu
1               5

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AAGAATTCAA RAAVARTGGG AYGG                        24

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
                                            -continued
AAGAATTCTC NARCCAYTCN GGCCA                                                    25

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Asp Xaa Asp Val Val Ser Lys Lys Gln Trp Asp Gly Leu Ile Pro Val
1               5                   10                  15

His Val Ser Tyr
            20
```